United States Patent [19]
Colegrove

[11] 3,966,618
[45] June 29, 1976

[54] CLARIFICATION OF XANTHAN GUM

[75] Inventor: George T. Colegrove, San Diego, Calif.

[73] Assignee: Merck & Co., Inc., Rahway, N.J.

[22] Filed: Oct. 10, 1974

[21] Appl. No.: 513,810

Related U.S. Application Data

[63] Continuation-in-part of Ser. No. 449,875, March 11, 1974.

[52] U.S. Cl. ............................ 252/8.55 D; 166/246; 195/7; 195/31 P
[51] Int. Cl.² ...................... C12B 1/00; E21B 43/22
[58] Field of Search ................ 195/31 P, 7, 4, 5, 65, 195/104, 66 R; 252/8.55 D, 8.5 C, 311; 260/209 R; 166/246

[56] References Cited
UNITED STATES PATENTS

| | | | |
|---|---|---|---|
| 3,119,812 | 1/1964 | Rogovin et al. | 195/31 P |
| 3,288,211 | 11/1966 | Johnston | 166/246 |
| 3,305,016 | 2/1967 | Lindblom et al. | 252/8.55 X |

*Primary Examiner*—Herbert B. Guynn
*Attorney, Agent, or Firm*—Donald J. Perrella; Hesna J. Pfeiffer; J. Jerome Behan

[57] ABSTRACT

Fermentation broths and other aqueous suspensions containing a dissolved xanthan gum and suspended solids resulting from the fermentation producing the xanthan gum are clarified by treatment with a minor amount of a protease enzyme. The injectivity of aqueous solutions containing xanthan gum so clarified is improved, in oil well flooding operations, over solutions not so treated.

1 Claim, No Drawings

CLARIFICATION OF XANTHAN GUM

This application is a continuation-in-part of pending U.S. patent application Ser. No. 449,875, filed Mar. 11, 1974.

Xanthan gums are hydrophilic polysaccharides which are obtained by the fermentation of appropriate nutrient media with microorganisms of the genus Xanthomonas. When dissolved in water in low concentration they impart a viscosity to the aqueous solution which is highly important in applications where it is desirable to suspend solid materials in the aqueous medium. One of the known uses of xanthan gums is in drilling fluids for oil wells and in oil well flooding operations. For the latter use, it is necessary for the aqueous vehicle to have the viscosity characteristics necessary to displace the oil deposits but also to be sufficiently fluid that it can be transferred and pumped satisfactorily.

In the commercial preparation of most xanthan gums, the solid xanthan is recovered by precipitation from the fermentation broth in which it is made. Because of the viscosity properties of the xanthan, it is not generally feasible to separate all extraneous fermentation solids before this precipitation step, so that the dried solid xanthan gum normally contains some water-insoluble solids such as nonviable bacterial cells and other cellular debris. These solids, of course, remain undissolved on solution of the xanthan in water. While this is not objectionable in many cases, it is a drawback in systems where a solution substantially free of undissolved solids is desired. For instance, it presents difficulties when xanthan gum is used in oil well flooding operations because the solids tend to plug the small pores in the rock formations where secondary and tertiary oil recovery operations are carried out. In addition to the plugging, undesirable pressure increases can result.

Methods evaluated for overcoming this problem have included treatment of the xanthan gum solution with caustic, and flocculation of the dead cells on an adsorbent such as clay. These are not completely acceptable because they are tedious, costly and/or impractical to carry out under use conditions. In oil well flooding operations, the user generally prepares an aqueous concentrate of xanthan gum containing from about 0.25 to about 1.5% by weight of xanthan gum. This concentrate may be held at ambient temperature for a period of hours or days. Shortly prior to injection of the solution into the well bore, the xanthan gum solution is diluted to "use" concentration of from about 200–2,000 ppm. Any methods developed for overcoming the problem of the extraneous solids in xanthan gum should be compatible with these field use conditions. Such methods are provided by the present invention.

It is an object of this invention to provide a method for clarifying aqueous solutions of xanthan gum. Another object is provision of a method for clarifying the whole fermentation broth or beer resulting from preparation of xanthan gum by fermentation of a nutrient medium with a xanthan-producing microorganism. Another object is provision of a method for removing fermentation cellular debris from xanthan gum solutions. A still further object is improving the suitability of xanthan gum solution for use in oil well flooding. An additional object is the method of using xanthan gum solutions having improved injectivity for oil well flooding. A further object is provision of a solid composition which will, on solution in water, provide clarification of the xanthan gum solution. Other objects will become clear from the following description of the invention.

In accordance with this invention, it has now been found that aqueous solutions of xanthan gum containing as suspended solids the fermentation cellular debris resulting from preparation of xanthan by fermentation can be clarified by treatment of such solutions or suspensions with minor amounts of a protease enzyme. Reference herein to aqueous solutions of xanthan gum is intended to include the whole fermentation broth containing xanthan obtained by fermentation of a nutrient medium with a xanthan producing microorganism (sometimes referred to herein as beer). In addition, it includes solutions obtained by addition of isolated xanthan gum to aqueous media and also to partially purified xanthan gum solutions. The enzyme treatment of this invention results in partial or complete elimination of the suspended cells and affords a clarified solution which has not lost its viscosity and which can be used, if desired, after appropriate dilution, without any further chemical or mechanical treatment.

The enzymes found suitable for use in this process alkaline proteases. The alkaline protease enzymes are generally produced by microorganisms of the genus Bacillus such as *B. subtilis*, *B. licheniformis*, *B. amyloliquifaciens* and *B. pumilis*, although alkaline proteases are also elaborated by species of Streptomyces such as *S. fradiae*, *S. griseus* and *S. rectus*. The source of the enzyme is not critical. Among the alkaline proteases useful for practicing the invention are those known as subtilisins, e.g. subtilisin Novo and subtilisin Carlsberg, and subtilopeptidase A and subtilopeptidase B. These alkaline protease enzymes and the methods of obtaining them are well known in the art, typical articles and discussions being "Microbial Proteases" by L, keay, Process Biochemistry, August 1971, page 17; "Enzyme Detergents" by Laggrith and Liss, Encyclopedia of Chemical Technology, 2d Ed., Supplement Vol., page 294; and "Microbiological Origins of Detergent Enzymes" by L. Campbell, Developments in Industrial Microbiology, Vol. 12, p. 24.

In order to achieve the solution clarification of the invention, aqueous solutions of xanthan gum (containing the extraneous, undesirable fermentation solids suspended therein) and preferably containing from about 0.25 to about 3.0% by weight of xanthan gum are mixed with the desired amount of protease enzyme, and the mixture allowed to stand or age as described hereinbelow. When a fermentation beer is to be treated or clarified, the xanthan gum concentration is preferably from about 2.0–2.5% by weight. If desired the beer may be diluted with water before enzyme treatment and in such event the final concentration is suitably in the range of about 1.0–1.5% by weight of gum. Furthermore, when aqueous solutions prepared from isolated xanthan gum are to be clarified, the gum concentration is conveniently from about 0.25 to about 1.5%, and preferably 0.5–1.0%, by weight.

Under the reaction conditions described herein, the protease enzyme degrades the solid cellular debris to water soluble compounds so that the aqueous xanthan gum solution is clarified. It should be appreciated that the solution may not necessarily become crystal clear. Some haze may remain but this is not detrimental to the efficiency or usefulness of the process since the resulting solution is sufficiently free of solids to overcome the drawbacks discussed above.

Only minor amounts of enzyme are necessary to effect the desired clarification. Generally, the aqueous xanthan gum solution is treated with from about 25–2,000 ppm. (parts per million of aqueous solution) of enzyme, and preferably with about 50–1000 ppm. As will be seen from the following detailed examples, this treatment leads to clarification of the solution (as determined by colorimeter measurements) and to improved filterbility or pumpability (as determined using a Millipore filter).

Enzyme concentration or potency is frequently expressed in terms of arbitrary units. Thus, Delft Units are a convenient expression of the ability of an alkaline protease enzyme to degrade casein.

The Delft Unit is an arbitrary unit defined as follows: If 1 milliliter of a 2 percent solution of an alkaline protease enzyme preparation gives a corrected ultraviolet absorbance of 0.40 under the following test conditions, the enzyme preparation is defined to have a protease activity of one thousand Delft Units per gram.

The Delft Unit activity of the alkaline protease is determined by the modified Kunitz' method (J. Gen. Physiol. 30, 291, 1947), as follows: 1.0 ml. of a 2 percent aqueous solution of casein (Hammarstein's) and 0.5 ml. of an NaOH buffer, pH 11.0, are mixed with 0.5 ml. of an enzyme solution. 2.0 ml. of the resulting mixture is allowed to incubate at 37°C. for 20 minutes, and then the reaction is stopped by the addition of 3.0 ml. of a 5 percent aqueous solution of trichloroacetic acid. The mixture is allowed to stand at 37°C. for a further 30 minutes, during which time the undigested casein precipitates. The precipitated casein is filtered off and the resulting filtrate is subjected to optical density determination at 275 m$\mu$. The optical density reading is corrected by the optical density reading obtained from a control in which no proteolysis has taken place, e.g., without enzyme.

Other units of measurement of enzyme activity are, of course, known in the art. Hemoglobin Units, for example, are frequently employed to define the enzyme potency of fungal proteases.

It is preferred to carry out the process of this invention using an alkaline protease enzyme and employing for the reaction from about 25 to about 60,000, and preferably from about 1500 to 20,000 Delft Units of alkaline protease per gram of xanthan gum. With the alkaline protease enzyme preparations described herein as suitable for practicing the invention, an enzyme level of about 30 Delft Units per gram of xanthan gum is obtained by employing the enzyme preparation at a level of 1 ppm. of aqueous solution containing 1.0% xanthan gum.

It will be understood by those skilled in the art that for the alkaline protease enzymes to be effective, the pH of the aqueous solution should be at about pH 7 or more alkaline. The aqueous solution of xanthan gum containing the alkaline protease enzyme is aged at pH 7 or higher (i.e. up to pH 12) for up to about 20–25 hours at temperatures of from about room temperature to about 140°F. (60°c.). When the higher temperatures are used, and under some conditions they are preferred, the optimum time will be shorter, e.g. about 1–2 hours at 135°F. (57°C.). Agitation is not essential, although where feasible the solution is stirred or agitated mildly or periodically to avoid undue settling of the solids and promote contact with the protease enzyme.

According to one aspect of the invention, the enzyme clarification is carried out at essentially neutral pH with alkaline protease. When a whole fermentation broth is used or when solid xanthan gum containing extraneous water-insoluble fermentation solids is used as starting material, a specific pH adjustment is usually unnecessary but if it should be desired, it can be accomplished by addition of a base such as ammonium hydroxide or an alkali metal hydroxide. The presence of other extraneous chemicals, such as for example chlorine or high salt concentration, which interfere with the enzymic activity of the proteases or degrade the enzyme, should, of course, be avoided.

As previously indicated, the whole fermentation broth (or beer) obtained in producing xanthan gum by fermentation of an appropriate aqueous nutrient medium with a xanthan-producing microorganism contains undissolved solids and cell debris in addition to the xanthan gum which is water soluble. According to a preferred aspect of the invention, either this whole fermentation broth or aqueous solutions of xanthan gum obtained by dissolving isolated gum in an aqueous vehicle are clarified by treating with an alkaline protease enzyme at a pH of from about 9–12, and at an elevated temperature of up to about 140°F. (60°C.).

When the enzyme-treated xanthan gum solutions of this invention are to be used in oil well flooding, an aqueous concentrate is first prepared containing about 0.25–1.5 weight percent of xanthan gum, and this is diluted prior to actual use with additional water or aqueous vehicle to a xanthan gum concentration of about 200–2,000 ppm., preferably about 300–1000 ppm. When the enzyme clarification has not been carried out on xanthan fermentation beer, it may be conducted in the field on the 0.25–1.5% aqueous concentrate. On dilution, there is thus obtained a clarified solution having the desired viscosity, and having substantially improved injectivity properties for use in the flooding operation.

In accordance with an additional aspect of this invention, there are provided solid formulations containing xanthan gum and an alkaline protease enzyme, which may be added directly to an aqueous vehicle, thereby eliminating the need for separate addition of the enzyme to a xanthan gum solution. These solid compositions are of particular interest when the enzyme clarification is to be carried out, for instance, at the site of an oil recovery operation. It is preferred that these solid compositions contain from about 5–20 parts of xanthan gum per part of protease enzyme. Thus, compositions are contemplated containing 85–95% by weight of xanthan gum and 15–5% by weight of enzyme. If a solid inert diluent or extender is used, the ratio of polysaccharide to enzyme should be maintained within the foregoing ranges.

Any of the known xanthan gums, which may also be described as Xanthomonas hydrophilic colloids, may be used in the practice of this invention. It is preferred to use the colloid produced by the bacterium *Xanthomonas campestris*, which compound and its preparation are fully described in U.S. Pat. No. 3,659,026, column 4.

Other Xanthomonas colloidal material (xanthan gum) may be prepared by repeating the procedure described in this patent for producing the *Xanthomonas campestris* colloid by using as the producing microorganism other known Xanthomonas bacteria i.e., *Xanthomonas carotate, Xanthomonas incanae, Xanthomonas begoniae, Xanthomonas malvacerum, Xanthomonas vesicatoria, Xanthomonas papavericola, Xanthomnonas*

*translucens, Xanthomonas vasculorum* and *Xanthomonas hederae* in place of the *Xanthomonas campestris*.

The following examples are given for the purpose of illustration and not by way of limitation.

Example 1

To 200 ml. of 1.0% aqueous solutions (in tap water and soft water) of xanthan gum produced by fermentation of *Xanthomonas campestris* there is added 100 ppm. of the alkaline protease enzyme ALCALASE (Trademark of Novo Industries A/S for the alkaline protease enzyme produced by *Bacillus licheniformis*). A similar solution of xanthan gum in tap water without added enzyme serves as a control. The mixtures are allowed to stand at room temperature for 4 days and then diluted with 3,800 ml. of water to a xanthan gum concentration of 500 ppm. The clarity of the diluted mixtures is determined using a Klett-Summerson photoelectric colorimeter having a No. 47 filter. The bacterial cell count in the diluted solutions is determined by standard methods, and the percent cell reduction recorded. The solutions are also filtered at room temperature through a Millipore filter having a 1.2 micron pore size, and the volume of filtrate obtained in a 5 minute filtration time measured. The results are set forth in Table I below.

TABLE I

|  | Control | Added Enzyme Tap Water | Soft Water |
|---|---|---|---|
| Colorimeter reading | 22 | 11 | 6 |
| Percent cell reduction |  | 89.5% | 94.8% |
| Millipore filtrate (5 minutes) | 49 ml. | 68 ml. | 92 ml. |

EXAMPLE 2

The effect of various concentrations of alkaline protease enzyme in clarifying xanthan gum solutions is determined as follows: to separate 200 ml. aliquots of 1% solution of xanthan gum (obtained via fermentation of *Xanthomonas campestris*) in tap water there is added ALCALASE enzyme at concentrations of 25, 50 and 500 ppm. The resulting mixtures are allowed to stand at room temperature for a total of 4 days. At the end of one hour and 24 hours small samples are removed from each of the mixtures and Klett-Summerson colorimeter readings made as described in Example 1 after dilution of the sample with water to a xanthan gum concentration of 500 ppm. At the conclusion of the 4 day period, the mixtures are diluted to a xanthan concentration of 500 ppm., and colorimeter and Millipore filtrate values determined as in Example 1. The results appear in Table II.

TABLE II

| Time | Control (no enzyme) | Colorimeter Readings 25 ppm. | 50 ppm. | 500 ppm. |
|---|---|---|---|---|
| 1 hr. | 32 | 30 | 27 | 22 |
| 24 hrs. | 29 | 22 | 20 | 18 |
| 4 days | 29 | 23 | 20 | 20 |
| Millipore filtrate (5 mins.) | 160 ml. | 164 ml. | 276 ml. | 320 ml. |

EXAMPLE 3

In an experiment conducted in the same manner as Example 2, a 1.0% solution of xanthan gum in tap water is treated with 200 ppm. ALCALASE enzyme, and the turbidity measured at various time intervals. The turbidity readings are taken as described in Example 1 after dilution of the mixture with water to a xanthan concentration of 500 ppm. The results appear in Table III.

TABLE III

| Time (hrs.) | Colorimeter Readings Control | Enzyme |
|---|---|---|
| 1 | 37 | 25 |
| 19 | 32 | 19 |
| 24 | 30 | 18 |
| 48 | 27 | 15 |
| 144 | 25 | 16 |

EXAMPLE 4

To be effective, the enzyme treatment should not substantially reduce viscosity of the xanthan gum solution. The effect of enzyme treatment on viscosity is determined by treating 200 ml. of a 0.6 % xanthan gum solution in tap water with 100 ppm. of ALCALASE enzyme. The mixture is held at room temperature for 4 days and then diluted with water to a xanthan concentration of 500 ppm. The diluted solution is filtered through a 1.2 micron Millipore filter (as in Example 1) to determine plugging tendency of the solution. A similar solution without added enzyme is the control. Viscosities are determined at room temperature using a Brookfield LVT viscometer with a U.L. adapter at 60 r.p.m. The results appear in Table IV.

TABLE IV

|  | Control | Added Enzyme |
|---|---|---|
| Millipore filtrate (5 minutes) | 29 ml. | 95 ml. |
| Viscosity before filtration | 4.8 cps | 4.6 cps |
| Viscosity after filtration | 4.1 cps | 4.4 cps |

EXAMPLE 5

The effect of temperature on the enzyme clarification is determined by addition of varying amounts of the alkaline protease subtilisin Carlsberg (marketed under the trademark MAXATASE by Chas. E. Pfizer) to 200 ml. of a 1.0% aqueous solution of xanthan gum produced by fermentation with *Xanthomonas campestris*. The mixtures are held at a temperature of 120°F. (49°c.) for 1 hour and then diluted with water to a xanthan gum concentration of 500 ppm. The clarity and filterability of the solution is determined as described in Example 1. The results are set forth in Table V.

TABLE V

|  | Enzyme in Concentrate (ppm.) 0 | 50 | 100 | 200 | 500 | 1000 |
|---|---|---|---|---|---|---|
| Colorimeter Reading | 29 | 11 | 9 | 10 | 10 | 10 |
| Millipore Filtrate (ml.) (5 mins.) | 136 | 250 | 382 | 376 | 640 | 960 |

EXAMPLE 6

Varying quantities of the alkaline protease enzyme marketed by the Enzyme Development Corporation under the trade name MAXAZYME are added to a 1.0% solution of xanthan gum (produced by *Xanthomonas campestris*). The mixtures are allowed to stand at room temperature for about 16 hours and then diluted to a concentration of 500 ppm. of xanthan gum. The clarity and filterability of the diluted solutions are measured as described in Example 1, the results appearing in Table VI below.

TABLE VI

|  | Enzyme in Concentrate (ppm) | | | | | |
| --- | --- | --- | --- | --- | --- | --- |
|  | 0 | 25 | 50 | 100 | 200 | 500 |
| Colorimeter Reading | 36 | 19 | 7 | 7 | 7 | 4 |
| Millipore Filtrate (ml.) (5 mins.) | 136 | 230 | 287 | 350 | 485 | 415 |

EXAMPLE 7

To an aqueous solution containing 750 ppm. of xanthan gum produced by fermentation of a nutrient medium with *Xanthomonas campestris* there is added 75 ppm. of alkaline protease produced by *Bacillus licheniformis* (ALCALASE, Novo Industries A/S). The mixture is allowed to stand at room temperature for 24 hours. Portions of this solution are then injected into sandstone cores having a permeability of 380 millidarcies, and the pressure rise determined as a function of pore volumes injected. Increase in pressure is a measure of the extent of core plugging by solids in the aqueous solution introduced with the xanthan gum. The control experiment is carried out in the same manner using a similar xanthan gum solution without added enzyme. The results appear in Table VII. The viscosity of the control solution is 14.7 cps, and of the enzyme treated solution 14.9 cps (Brookfield LVT Viscometer with a U.L. adapter, 6 r.p.m., room temperature).

TABLE VII

|  | Pore Volumes (ml.) | Pressure (psi) |
| --- | --- | --- |
| 1) 750 ppm xanthan gum 75 ppm enzyme | 2.3 | 2.0 |
|  | 4.5 | 2.2 |
|  | 7.3 | 2.25 |
|  | 10.9 | 2.5 |
|  | 18.0 | 2.5 |
|  | 23.6 | 2.9 |
|  | 28.8 | 3.0 |
|  | 33.6 | 3.25 |
|  | 38.9 | 3.4 |
|  | 42.6 | 3.6 |
| 2) 750 ppm. xanthan gum no enzyme | 2.8 | 3.2 |
|  | 5.6 | 3.4 |
|  | 8.9 | 4.1 |
|  | 12.1 | 4.4 |
|  | 15.5 | 4.8 |
|  | 22.0 | 5.25 |
|  | 29.9 | 6.25 |
|  | 31.8 | 6.3 |
|  | 39.3 | 6.5 |
|  | 45.1 | 7.0 |

In the foregoing examples the colorimeter and Millipore filter readings are determined as started in Example 1; the xanthan gum used is that produced by the Kelco Company, San Diego, California, under the trade name KELZAN MF.

The starting material used in Examples 8-13, inclusive, is whole fermentation broth (beer) obtained by growing a *Xanthomonas campestris* microorganism in an aqueous nutrient medium containing a source of carbohydrate, a protein supplement and an inorganic nitrogen source. The finished broth contains xanthan gum biopolymer at a concentration of about 22 to 24 mg. per ml.

EXAMPLE 8

To 500 ml. (500 grams) of fermentation broth there is added sufficient 1N sodium hydroxide solution to raise the pH to 11.0. The resulting mixture is maintained at 120°F. (49°C.) for 4 hours.

EXAMPLE 9

To 500 ml. (500 g.) of xanthan gum fermentation broth there is added 0.5 g. (165,000 Delft Units) of Maxazyme alkaline protease enzyme at 120°F. (49°C.). The resulting mixture is maintained for 4 hours at 120°F. (49°c.).

EXAMPLE 10

To 500 ml. (500 g.) of xanthan fermentation broth there is added 0.5 g. (165,000 Delft Units) of Maxazyme alkaline protease enzyme. The pH of the resulting mixture is then adjusted from essentially neutral to 11.0 with 1N sodium hydroxide solution, the resulting mixture heated to 120°F. (49°C.) and maintained at that temperature for 4 hours.

EXAMPLE 11

To 500 ml. (500 g.) of xanthan fermentation broth there is added 0.15 g. of Maxazyme alkaline protease enzyme. This affords a concentration of 300 ppm. of enzyme in the solution (4300 Delft Units per gram of xanthan gum). The pH of the mixture is adjusted from essentially neutral to 9.0 by the addition of 1N sodium hydroxide solution. The mixture is heated to 85°F. (30°C.) and maintained at that temperature for 4 hours. The pH is then raised to 12.0 by the addition of additional 1N sodium hydroxide and the resulting solution maintained at 85°F. (30°C.) for 3 hours.

EXAMPLE 12

To 500 ml. (500 grams) of xanthan gum fermentation broth there is added 0.05 g. of Maxazyme alkaline protease enzyme. This affords an enzyme concentration in a solution of 100 ppm. (1440 Delft Units per gram of xanthan gum). The pH of the mixture is adjusted from essentially neutral to 9.0 by the addition of 1N potassium hydroxide, the mixture heated to 110°F. (43°C.) and maintained at this temperature for 6 hours. The pH of the solution is then raised to 12.0 by the addition of 1N potassium hydroxide and the mixture held at 110°F. (43°C.) for 1 hour.

EXAMPLE 13

The method of Example 12 is repeated except that 0.025 g. of enzyme are used, affording a solution concentration of 50 ppm. (720 Delft Units per gram of xanthan gum.

At the completion of the treatments described in Examples 8-13 above, the mixtures are neutralized to pH 5.5 with 1N hydrochloric acid, and cooled to about 70°F. (21°C.). To the resulting mixture is added 1,000 ml. of 2-propanol. The alcohol treatment precipitates the xanthan gum. The mixture is filtered and the solids are dried by heating at 140°F. (60°C.) for about 5 hours. The solids are then milled to give uniform particle size. Clarity is determined by preparing a 1% aqueous solution of the xanthan gum and then diluting to a concentration of 500 ppm. of xanthan gum. The clarity of the diluted mixture is then determined using a Klett Summerson photoelectric Colorimeter having a number 47 filter. The results are set forth in Table VIII below.

TABLE VIII

| Example No. | Klett Reading |
|---|---|
| 8 | 29 |
| 9 | 15 |
| 10 | 0 |
| 11 | 0 |
| 12 | 4 |
| 13 | 9 |
| Control, no enzyme treatment | 35 |

EXAMPLE 14

To 400 ml. (400 g.) of xanthan gum whole fermentation broth there is added 0.132 g. of Esperase alkaline protease enzyme (produced by Novo Industries) and 0.4 g. of sodium tripolyphosphate. This affords an enzyme concentration of 330 ppm. (.03 Anson Units; 6600 Delft Units) per gram of xanthan gum. The pH of the mixture is adjusted from essentially neutral to 9.5 with 1N sodium hydroxide. The mixture is heated to 120°F. (49°C.) and maintained at this temperature for 6 hours. It is then adjusted to pH 5.5 by the addition of 1N HCl. The mixture is cooled to about room temperature, and the xanthan gum precipitated by the addition with stirring of 800 ml. of 2-propanol. The solid xanthan gum product is recovered by filtration and dried. Under the test conditions described above, the product has a Klett reading of 0 at a concentration of 500 ppm. of xanthan gum. Under the same test conditions the control xanthan gum (no enzyme treatment) has a Klett reading of 35.

EXAMPLE 15

To 500 ml. (500 g.) of xanthan gum fermentation whole broth there is added 0.25 g. of Maxazyme alkaline protease enzyme to afford an enzyme concentration of 500 ppm. (7170 Delft Units per gram of xanthan gum). The mixture is adjusted to pH 9.0 by adding 1N potassium hydroxide. It is heated to 135°–140°F. (57°–60°C.) and maintained at this temperature for 1¾ hours. At the end of this time the xanthan gum is recovered as described above and the clarity determined, also as described above. The Klett reading is 0.

EXAMPLE 16

A 2.0% solution of a commercial sample of xanthan gum (available from the Kelco Company, San Diego, California, under the trade-mark KELZAN MF) is prepared in tap water. 250 ppm. of alkaline protease enzyme is added thereto with good agitation and the pH was adjusted to 9.0 with dilute sodium hydroxide. The temperature is raised to 115°F. (46°C.) and mixing continued for 4 hours. The pH is then raised to 11.5 with sodium hydroxide and the mixture held an additional three hours at the same temperature. The pH is then lowered to 5.5 with dilute hydrochloric acid and the xanthan gum is precipitated with isopropanol as described above, dried and milled. The treated xanthan gum is then compared with the untreated sample for clarity and filtration properties. Using the Klett-Summerson colorimeter with No. 47 filter the untreated sample at a concentration of 500 ppm. xanthan gum, gives a haze reading of 36 while the enzyme treated sample produces a haze reading of 1.0. The flow rate through a 1.2 micron Millipore filter is 750 ml./minute for the enzyme treated material and 450 ml./minute for the control.

Any departure from the above description which conforms to the present invention is intended to be included within the scope of the claims.

I claim:
1. A solid composition comprising from about 85–95% by weight of solid xanthan gum containing cellular fermentation solids and about 5–15% by weight of an alkaline protease enzyme.

* * * * *